June 25, 1974 TAKEO YUGE Plant Pat. 3,580
AZALEA PLANT
Filed Jan. 15, 1973
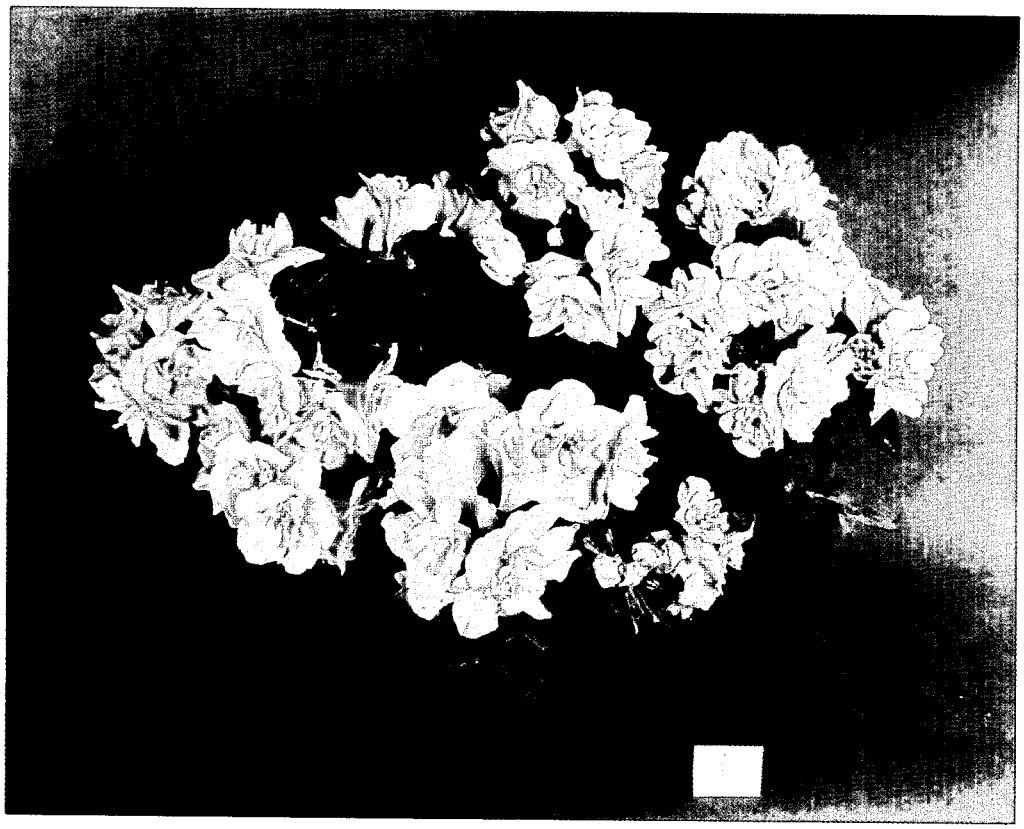

United States Patent Office

Plant Pat. 3,580
Patented June 25, 1974

3,580
AZALEA PLANT

Takeo Yuge, Altadena, Calif., assignor to Geo. J. Ball, Inc., West Chicago, Ill.

Filed Jan. 15, 1973, Ser. No. 323,917
Int. Cl. A01h 5/00
U.S. Cl. Plt.—55 1 Claim

ABSTRACT OF THE DISCLOSURE

A new variety of azalea plant for potted plant culture characterized by its early spring flowering habit and its profuse production of large pink blossoms on a compact and profusely branched plant form.

BACKGROUND OF THE INVENTION

My new variety of pink azalea was discovered by me as a seedling of Kaho × Jean Haerens, each unpatented, developed by me at Altadena, Calif., in the course of breeding efforts carried on with the objective of producing new and improved azalea plant varieties for the commercial market. This plant was selected for propagation and test because of its profuse production of large true pink flowers and its compact much branched growth habit. Asexual propagation of this new plant by vegetative cuttings carried on by me and under my direction at Altadena, Calif., has demonstrated the new plant to have its distinctive characteristics firmly fixed and running true from generation to generation and propagation on a commercial scale is now being carried on at Salem, Ore., and at San Fernando, Calif.

DESCRIPTION OF THE DRAWING

This new variety of azalea plant is illustrated by the accomplanying full color photographic drawing which shows a potted plant in full bloom, the colors shown being as nearly true as can be obtained by conventional photographic procedures.

DESCRIPTION OF THE NEW PLANT

The following is a detailed description of my new azalea plant, with color designations according to the Horticultural Colour Chart issued by the British Colour Council in collaboration with The Royal Horticultural Society.

*The plant*

Origin: Seedling.
Parentage: Seed parent—Kaho (unpatented). Pollen parent—Jean Haerens (unpatented).
Classification: Hybrid azalea.
Form: Compact potted plant.
Height: Up to 8 inches.
Growth: Vigorous and compact.
Branching: Profusely branched with limber but upright character.
Foliage: Quantity—abundant.
*Leaf shape.*—Obovate to elliptical. Size: Variable up to to 2¾ inches long. Texture: Leathery and strigose with smooth edges. Color: Upper side—Parsley Green 00962; under side—Spinach Green 0960/3. Petioles: Up to ½ inch long. Ribs and veins: Netted.

*The bud*

Form: Elliptical, very long to ¾ inch and pointed.
Size: Large, ¾ inch in diameter.
Opening: Slowly.

Color: When sepals first divide—Close to Spiraea Red 025/1. When petals begin to unfurl—Solferino Purple 26/2.
Sepals: Upstanding.
*Form.*—Obovate to spatulate.
*Color.*—Inside—Fern Green 0862 at tip becoming progressively paler to a white base. Outside—Fern Green 0862 at tip becoming Pod Green, 061 to almost white at base.
Calyx:
*Shape.*—Pear shaped and 5 lobbed.
*Size.*—Small and moderately broad.
*Aspect.*—Smooth but almost indiscernibly hairy. Calyx splits.

*The flower*

Blooming habit: Intermittent. Flowering once and profusely in the early spring.
Size: Large. 2¾ to 3 inches in diameter and 1½ inches in depth.
Borne: In clusters.
Shape: When bloom first opens—Pointed high center, becoming flat but with upright center petals.
Petalage: 12 to 15 in number, fused at base.
*Form.*—Semi-double funnel with obovate base, acute tip and gently undulate margin.
*Arrangement.*—Connate.
*Color.*—Outer petals—Solferino Purple 26/2, flecked and shaded toward base with base of Rose Red 724/1. Inside petals—Solferino Purple 26/2 flecked and blotched with Rose Red 724/1. Reverse side—Solferino Purple 26/2.
*Texture.*—Soft. Appearance: Satiny.
*Discoloration.*—Very slight tinting.
Petaloids: 2 to 3 in number, ¾ inch long.
*Color.*—Solferino Purple 26/2.
Peduncle: Sturdy, upright, 5/16 inch long.
*Color.*—Lettuce Green 861/2.
Persistence Petals hang on and dry.
Fragrance Slight to moderate.
Disease resistance: Resists all common diseases prevalent in the areas where this plant has been grown.
Lasting quality Very long lasting—in excess of two weeks.

*Reproductive organs*

Stamens:
*Anthers.*—Very few, 1/16 inch long, often absent.
*Filaments.*—½ to 9/16 inch long. Color—Near white.
*Pollen.*—None observed.
Pistils: Single, with 1½ inch long style of Spiral Red 0023/1 color.
Stigma: Color—Fern Green 0862/1.
Ovary: Superior, with very hirsute wall.

This azalea plant is particularly distinguished by its early blooming habit and the true pink coloration of its flowers, this combination of characteristics affording a definite market advantage. This plant is also outstanding because of its vigorous and spreading growth providing abundant foliage topped with a profusion of relatively large flowers.

The Claim:

1. A new and distinct variety of pink azalea plant substantially as herein shown and described, characterized by its vigorous and spreading growth, its profuse production of large pink blossoms and its early spring blooming habit.

No references cited.

ROBERT E. BAGWILL, Primary Examiner